(12) United States Patent
Holsheimer

(10) Patent No.: US 6,892,097 B2
(45) Date of Patent: May 10, 2005

(54) METHOD OF PREPARING NEURAL TISSUE OF THE BRAIN FOR SUBSEQUENT ELECTRICAL STIMULATION

(75) Inventor: Jan Holsheimer, Oldenzaal (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/393,204

(22) Filed: Mar. 20, 2003

(65) Prior Publication Data

US 2004/0044379 A1 Mar. 4, 2004

Related U.S. Application Data

(62) Division of application No. 10/140,387, filed on May 7, 2002, which is a continuation of application No. 09/591,957, filed on Jun. 12, 2000, now abandoned, which is a division of application No. 09/070,264, filed on Apr. 30, 1998, now abandoned.

(51) Int. Cl.$^7$ ................................................ A61N 1/36
(52) U.S. Cl. ...................................................... 607/46
(58) Field of Search ........................... 607/1–3, 46, 44, 607/45, 116, 67, 68, 70, 72

(56) References Cited

U.S. PATENT DOCUMENTS

| | | |
|---|---|---|
| 3,724,467 A | 4/1973 | Avery et al. |
| 4,608,985 A | 9/1986 | Crish et al. |
| 5,095,905 A | 3/1992 | Klepinski |
| 5,282,468 A | 2/1994 | Klepinski |
| 5,501,703 A | 3/1996 | Holsheimer et al. |
| 5,713,922 A | 2/1998 | King |
| 5,925,070 A * | 7/1999 | King et al. ................... 607/67 |
| 6,421,566 B1 | 7/2002 | Holsheimer |

FOREIGN PATENT DOCUMENTS

| | | |
|---|---|---|
| EP | 0974375 A2 | 1/2000 |
| FR | 2422411 | 11/1979 |
| WO | WO 95/19804 A1 | 7/1995 |

OTHER PUBLICATIONS

Brindley, G.S. et al., "A Technique for Anodally Blocking Large Nerve Fibers Through Chronically Implanted Electrodes", *Journal of Neurology, Neurosurgery and Psychiatry*, vol. 43, 1980, pp. 1083–1090.

Deurloo, K.E.I. et al., "Optimization of Inactivating Current Waveform for Selective Peripheral Nerve Stimulation", *Proc. 2nd Ann. Conference on Int. Funct. Electrostim Soc.*, 1997, Vancouver, pp. 237–238.

Deurloo, K.E.I. et al., "Transverse Tripolar Stimulation for Selective FNS", *18th Annual International Conference of the IEEE Engineering in Medicine & Biology Society*, 1996, 2 pgs.

Grill, Warren M. et al., "Stimulus Waveforms for Selective Neural Stimulation", *IEEE Engineering in Medicine & Biology*, vol. 14, Jul.–Aug. 1995, pp. 375–385.

(Continued)

*Primary Examiner*—George R. Evanisko
(74) *Attorney, Agent, or Firm*—Medtronic, Inc.; Stephen W. Bauer

(57) ABSTRACT

Methods are disclosed of preparing neural tissue of the brain for subsequent electrical stimulation. For example, first, second and third electrodes may be placed in close proximity to tissue of a patient's brain. A hyperpolarizing electrical pre-pulse may be applied to the tissue through the first electrode wherein the tissue is more susceptible to subsequent electric stimulation, or a depolarizing electrical pre-pulse may be applied to the tissue through the first electrode wherein the tissue is less susceptible to subsequent electric stimulation. Other exemplary embodiments are also disclosed.

59 Claims, 6 Drawing Sheets

OTHER PUBLICATIONS

Struuk, J.J. et al., "Transverse Tripolar Spinal Cord Stimulation: Theoretical Performance of a Dual Channel System", *Medical & Biological Engineering & Computing*, Jul. 1996, pp.273–279.

Grill, Warren M. et al., "Inversion of the Current–Distance Relationship by Transient Depolarization", *IEEE Transactions on Biomedical Engineering*, vol. 44, No. 1, Jan. 1997, pp. 1–9.

Mullett, Keith R. et al., "Design and Function of Spinal Cord Stimulation—Theoretical and Developmental Considerations", *Patn Digest*, vol. 1, 1992, pp. 281–287.

Melzack, Ronald et al., "Pain Mechanisms: A New Theory", *Science*, vol. 150, No. 3699, Nov. 1965, pp. 971–979.

Struuk, Johannes J. et al., "Excitation of Dorsal Root Fibers in Spinal Cord Stimulation: A Theoretical Study", *IEEE Trans. Biomed. Eng.*, vol. 40, Jul. 1993, pp. 632–639.

Holsheimer, J. et al., "MR Assessment of the Normal Position of the Spinal Cord in the Spinal Canal", *Amer. J. Neuroradiol.*, vol. 15, May 1994, pp. 951–959.

Pang, Zi–Ping et al., "Selective Activation of Small Motor Axons by Quasitrapezoidal Current Pulses", *IEEE Trans. on Biomed. Eng.*, vol. 38, No. 2, Feb. 1991, pp. 168–174.

Wesselink, Wilbert et al., "Spinal Cord Stimulation: Fiber Diameters in the Dorsal Columns Modeled From Clinical Data", *Inst. for Biomed. Tech., 18$^{th}$ Ann. Intl. Conference of the IEEE Eng. in Med. & Biol. Soc.*, Oct.–Nov. 1996, 4 pgs.

Neumcke, B. et al., "A Comparison of Sodium Currents in Rat and Frog Myelinated Nerve: Normal and Modified Sodium Inactivation", *J. Physiol.*, vol. 382, 1987, pp. 175–191.

Deurloo, K.E.I. et al., "Transverse Tripolar Stimulation of Peripheral Nerve: A Modeling Study of Spatial Selectivity", *Medical & Biological Engineering & Computing*, Jan. 1998, pp. 66–74.

\* cited by examiner

METHOD OF PREPARING NEURAL TISSUE OF THE BRAIN FOR SUBSEQUENT ELECTRICAL STIMULATION

RELATED APPLICATION

This application is a divisional of prior application Ser. No. 10/140,387, filed May 7, 2002, which in turn is a continuation of application Ser. No. 09/591,957, filed Jun. 12, 2000, now abandoned, which is a divisional of application Ser. No. 09/070,264, filed Apr. 30, 1998, now abandoned.

BACKGROUND OF THE INVENTION

1. Field of the Invention

This invention relates to an apparatus and method for electrically stimulating neural tissue including, but not limited to, a spinal cord. More specifically, this invention relates to an apparatus and method for applying a precursor electrical pulse to neural tissue prior to a stimulation pulse with the first pulse "conditioning" the tissue for the application of the stimulation pulse.

2. Description of the Prior Art

Nerve cells in the brain and the spinal cord have a variety of shapes and sizes. A typical nerve cell has the shape shown in FIG. 1 generally labeled 1. The classical parts of nerve cell 1 are the cell body 2, the dendritic tree 3 and the axon 4 (including its terminal branches). Nerve cells convey information to other cells at junctions called synapses.

An important property of the nerve cell is the electrical potential that exists across the cell's outer membrane 5. Normally, when cell 1 is at rest, the inside 6 of cell 1 is 70–80 mV negative with respect to the outside 7 of cell 1. As shown in FIG. 2, cell 1 has chemical pumps 8 imbedded in the cell membrane 5. Pumps 8 consume energy to move sodium ions 9 outside and potassium ions 10 into the cell 1 to maintain the concentration gradients and therefore the electrical potential difference across membrane 5.

The membrane 5 of the axon 4 has specific dynamic properties related to its function to transmit information. In man, like in other mammals, it contains sodium channels 11 and leakage channels 12. Membrane 5 has a voltage and time dependent sodium conductivity that is related to the number of open sodium channels. Channels 11 open and close in response to changes in the potential across the membrane 5 of the cell 1. When the membrane 5 is in its resting state (70–80 mV negative at the inside), only few sodium channels 11 are open. However, when the electrical potential across membrane 5 is reduced (membrane depolarization) to a value called the excitation threshold, the sodium channels 11 open up allowing sodium ions 9 to rush in (excitation). As a result, the electrical potential across membrane 5 changes by almost 100 mV, so that the inside 6 of the axon 4 gets positive with respect to the outside 7.

After a short time the sodium channels 11 close again and the resting value of the membrane potential is restored by the flow of ions through the leakage channels 12. This transient double reversal of the potential across the membrane 5 is named "action potential". The action potential, which is initiated at a restricted part of membrane 5, also depolarizes adjacent portions of the membrane 5 up to their excitation threshold. Channels 11 in these portions begin to open, resulting in an action potential at that portion of the membrane 5 which then affects the next section of membrane 5 and so on and so on. In this way the action potential is propagated as a wave of electrical depolarization along the length of the axon 4 (FIG. 3).

After an action potential has been generated, there is a refractory period during which nerve cell 1 cannot generate another action potential. The sodium channels 11 do not open again when the membrane 5 is depolarized shortly after its excitation. The effect of the refractory period is that action potentials are discrete signals. Trains of propagating action potentials transmit information within the nervous system, e.g. from sense organs in the skin to the spinal cord and the brain.

There are two categories of nerve fibers that carry sensory information from remote sites to the spinal cord, small diameter afferent nerve fibers 13 and large diameter afferent nerve fibers 14. Generally speaking, the small diameter afferent nerve fibers 13 carry pain and temperature information to the spinal cord while the large diameter afferent nerve fibers 14 carry other sensory information such as information about touch, skin pressure, joint position and vibration to the spinal cord. As shown in FIG. 4, both the small and large diameter afferent nerve fibers 13, 14 enter the spinal cord 16 at the dorsal roots 17. Only large diameter nerve fibers 14 contribute branches to the dorsal columns 15.

Melzack and Wall published a theory of pain which they called the "gate control theory." (R. Melzack, P. D. Wall, Pain Mechanisms: A new theory. *Science* 1965, 150:971–979) They reviewed past theories and data on pain and stated that there seems to be a method to block pain at the spinal level. Within the dorsal horn of gray matter of the spinal cord, there is an interaction of small and large diameter afferent nerve fibers 13, 14 through a proposed interneuron. When action potentials are transmitted in the large diameter afferent nerve fibers 14, action potentials arriving along small diameter nerve fibers 13 (pain information) are blocked and pain signals are not sent to the brain. Therefore, it is possible to stop pain signals of some origins by initiating action potentials in the large diameter fibers. The type of pain that can be blocked by such activity is called neuropathic pain. Chronic neuropathic pain often results from damage done to neurons in the past.

Spinal Cord Stimulation (SCS) is one method to preferentially induce action potentials in large diameter afferent nerve fibers 14. These fibers 14 bifurcate at their entry in the dorsal columns 15 into an ascending and a descending branch (dorsal column fiber), each having many ramifications into the spinal gray matter to affect motor reflexes, pain message transmission or other functions. Only 20% of the ascending branches reach the brain (for conscious sensations).

Action potentials in the large diameter nerve fibers 14 are usually generated at lower stimulation voltages than action potentials in small diameter nerve fibers 13. While the dorsal roots 17 could be stimulated to cause action potentials in the large diameter afferent nerve fibers 14, stimulation there can easily cause motor effects like muscle cramps or even uncomfortable sensations. A preferred method is to place electrodes near the midline of spinal cord 16 to limit stimulation of the nerve fibers in dorsal root 17.

Today, SCS systems use cylindrical leads or paddle-type leads to place multiple electrodes in the epidural space over the dorsal columns 15. Often the surgeon will spend an hour or more to position the leads exactly, both to maximize pain relief and to minimize side effects. One of the current problems with SCS is the preferential stimulation of nerve fibers in the dorsal roots (dorsal root nerve fibers) instead of nerve fibers in the dorsal columns (dorsal column fibers) especially at mid-thoracic and low-thoracic vertebral levels. This is in part because the largest dorsal root fibers 14 have larger diameters than the largest nearby dorsal column fibers. Other factors contributing to the smaller stimulus needed to excite dorsal root fibers are the curved shape of the dorsal root fibers and the stepwise change in electrical conductivity of the surrounding medium at the entrance of a dorsal root into the spinal cord (J. J. Struijk et al., *IEEE Trans Biomed Eng* 1993, 40:632–639). Stimulation of fibers in one or more dorsal roots results in a restricted area of paresthesia. That is, paresthesia is felt in only a few dermatomes (body zones innervated by a given nerve). In contrast, dorsal column stimulation results in paresthesia in a large number of dermatomes.

One approach to suppress the activation of dorsal root fibers and thereby favor dorsal column stimulation has been the application of an electric field to the tissue where the shape of the electric field is changeable and, as a result, where the location of the electric field in the tissue is steerable. This technique has been described in U.S. Pat. No. 5,501,703 entitled Multichannel Apparatus For Epidural Spinal Cord Stimulation that issued Mar. 26, 1996 with Jan Holsheimer and Johannes J. Struijk as inventors. As described in this patent, the electric field produced by electrodes described in the patent is shaped and steered to preferentially activate dorsal column fibers instead of dorsal root fibers. The invention is based on the principle that nerve fibers are depolarized (and eventually excited) when a nearby electrode is at a negative potential, while the opposite (hyperpolarization) occurs near electrodes at a positive potential. A negative electrode is named a cathode, because it attracts ions with a positive charge (cations). A positive electrode is named an anode, because it attracts negative ions (anions).

In practice, electrodes are typically placed epidurally. It appears that where the distance between the epidurally located electrodes and the spinal cord is large, such as at the mid-thoracic and low-thoracic levels, the method described in the '703 patent may still not sufficiently favor stimulation of the dorsal column fibers over dorsal root fibers in a number of patients (J. Holsheimer et al., *Amer J Neuroradiol* 1994, 15:951–959). The relatively large dorsal root fibers may still generate action potentials at lower voltages than will nearby dorsal column fibers. As a result, the dorsal column fibers that are desired to be stimulated have a lower probability to be stimulated than the dorsal root fibers, which are not desired to be stimulated and which produce the undesirable side effects noted above. Therefore, a different or concurrent approach may be needed.

Grill and Mortimer (*IEEE Eng Med Biol Mag* 1995, 14:375–385) have shown that applying an appropriate prepulse, sub-threshold to the production of an action potential, to neural tissue can make the nerve fibers either more or less excitable. More particularly, when an appropriate sub-threshold depolarizing (cathodic) pre-pulse (DPP) is applied to neural tissue in advance of a cathodic stimulation pulse, the nerve membrane 5 will be slightly depolarized, causing a reduction of the (small) number of open sodium channels 11 (FIG. 2). As a result, the excitation threshold of the axon 4 will increase and a stronger stimulus is needed to evoke an action potential than without a DPP. Conversely, when an appropriate hyperpolarizing (anodic) pre-pulse (HPP) is applied to neural tissue in advance of a cathodic stimulation pulse, the nerve membrane 5 will be hyperpolarized, causing an increase of the number of open sodium channels 11. As a result, the excitation threshold of the axon 4 will decrease and a weaker stimulus is needed to initiate an action potential than without an HPP.

The teaching of Grill and Mortimer is incorporated herein in its entirety. HPP make nerve fibers more excitable while DPP make nerve fibers less excitable. Grill and Mortimer have shown that for a 100 $\mu$s cathodic pulse without HPP or DPP and having a sub-threshold amplitude, the application of an (anodic) HPP pulse prior to the previously sub-threshold cathodic pulse can enable the identical 100 $\mu$s pulse to now trigger an action potential. In particular, if a 400 $\mu$s HPP of 90% of the threshold amplitude for a 500 $\mu$s pulse, but opposite in sign, precedes the 100 $\mu$s pulse of sub-threshold amplitude, the 100 $\mu$s pulse will create an action potential in the nerve fiber.

Conversely, Grill and Mortimer have shown that for a 100 $\mu$s cathodic pulse without HPP or DPP and having a sufficient amplitude (supra-threshold) to trigger an action potential, the application of a (cathodic) DPP pulse prior to the previously supra-threshold cathodic pulse can cause the identical 100 $\mu$s pulse to now be sub-threshold. In particular, if a 400 $\mu$s DPP of 90% of threshold amplitude for a 500 $\mu$s pulse and of the same sign precedes the 100 $\mu$s pulse of threshold amplitude, the 100 $\mu$s pulse will now be sub-threshold and will not create an action potential in the nerve fiber.

Deurloo et al. (Proc. $2^{nd}$ Ann Conf Int Funct Electrostim Soc, 1997, Vancouver, pp. 237–238) have recently shown that the effect of DPP can be obtained more efficiently when using an exponentially increasing cathodic current instead of a rectangular current shape.

SUMMARY OF THE INVENTION

A system and method is described for preferentially stimulating dorsal column fibers while avoiding stimulation of dorsal root fibers. The invention applies hyperpolarizing (anodic) pre-pulses (HPP) and depolarizing (cathodic) pre-pulses (DPP) to neural tissue, such as spinal cord tissue, through a lead placed over the spinal cord having the electrodes arranged on a line approximately transverse to the axis of the spine. To increase the threshold needed to stimulate dorsal root fibers, the anodal pulse given by each lateral contact of the electrode, is preceded by a DPP. The cathodic pulse, given simultaneously by the central electrode contact is preceded by an HPP, thereby reducing the stimulation threshold for the dorsal column fibers.

It is therefore a primary object of the invention to provide a system and method for treating pain by spinal cord stimulation (SCS) by preferentially stimulating dorsal column fibers over dorsal root fibers.

It is another primary object of the invention to provide a system and method for electrically stimulating the spinal cord by preferentially stimulating dorsal column fibers over dorsal root fibers.

It is another primary object of the invention to provide a system and method for electrically and preferentially stimulating selected regions of the brain and peripheral nerves.

It is another object of the invention to provide a system and method for treating pain by SCS by preferentially stimulating dorsal column fibers over dorsal root fibers that is easy to use.

It is another object of the invention to provide a system and method for electrically stimulating the spinal cord by preferentially stimulating dorsal column fibers over dorsal root fibers that is easy to use.

These and other objects of the invention will be clear to those skilled in the art from the description contained herein and more particularly with reference to the Drawings and the Detailed Description of the Invention where like elements, wherever referenced, are referred to by like reference numbers.

DETAILED DESCRIPTION OF THE INVENTION

Figure 1:
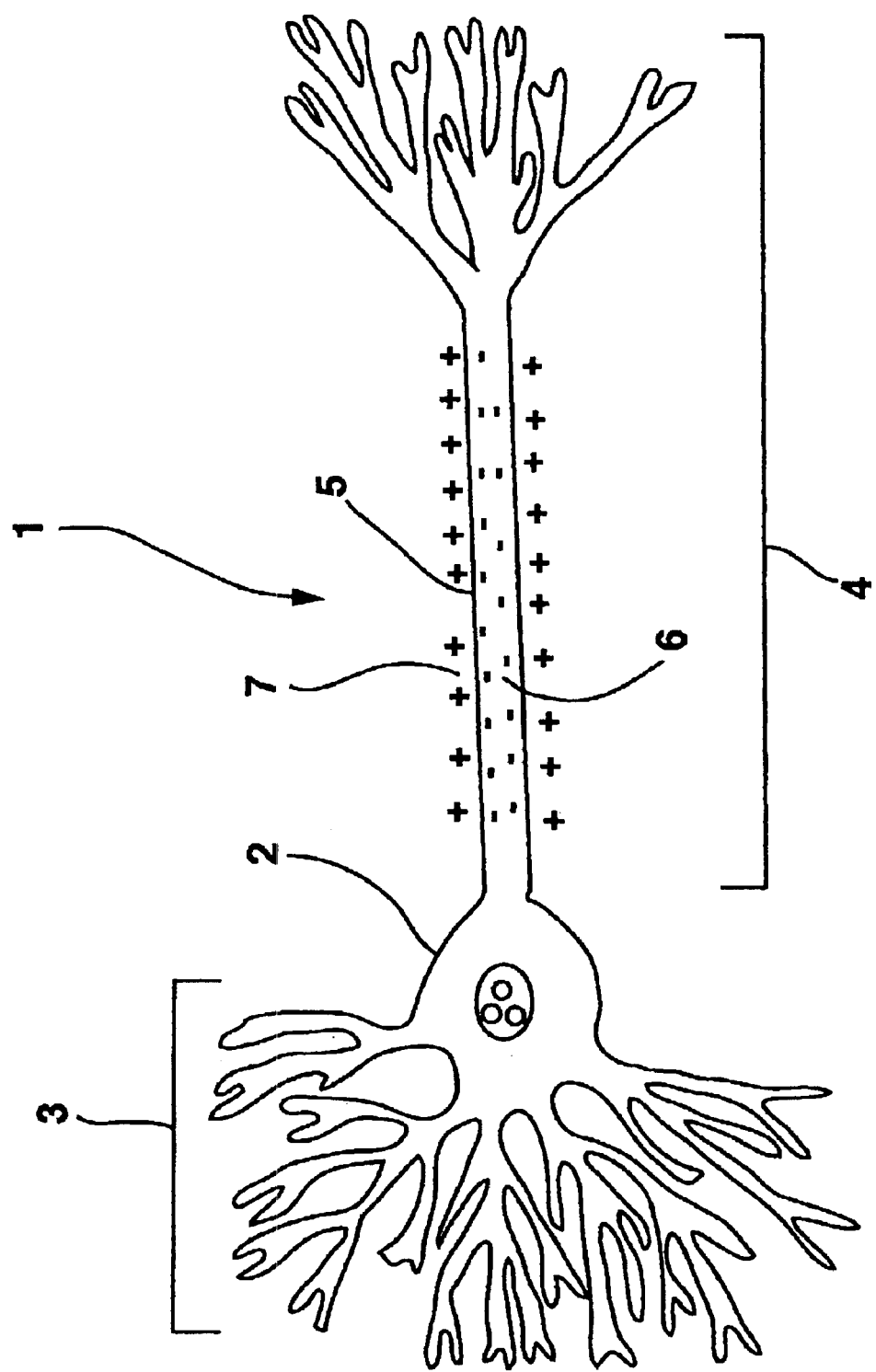
FIG. 1 is a schematic view of a nerve cell.
Figure 2:
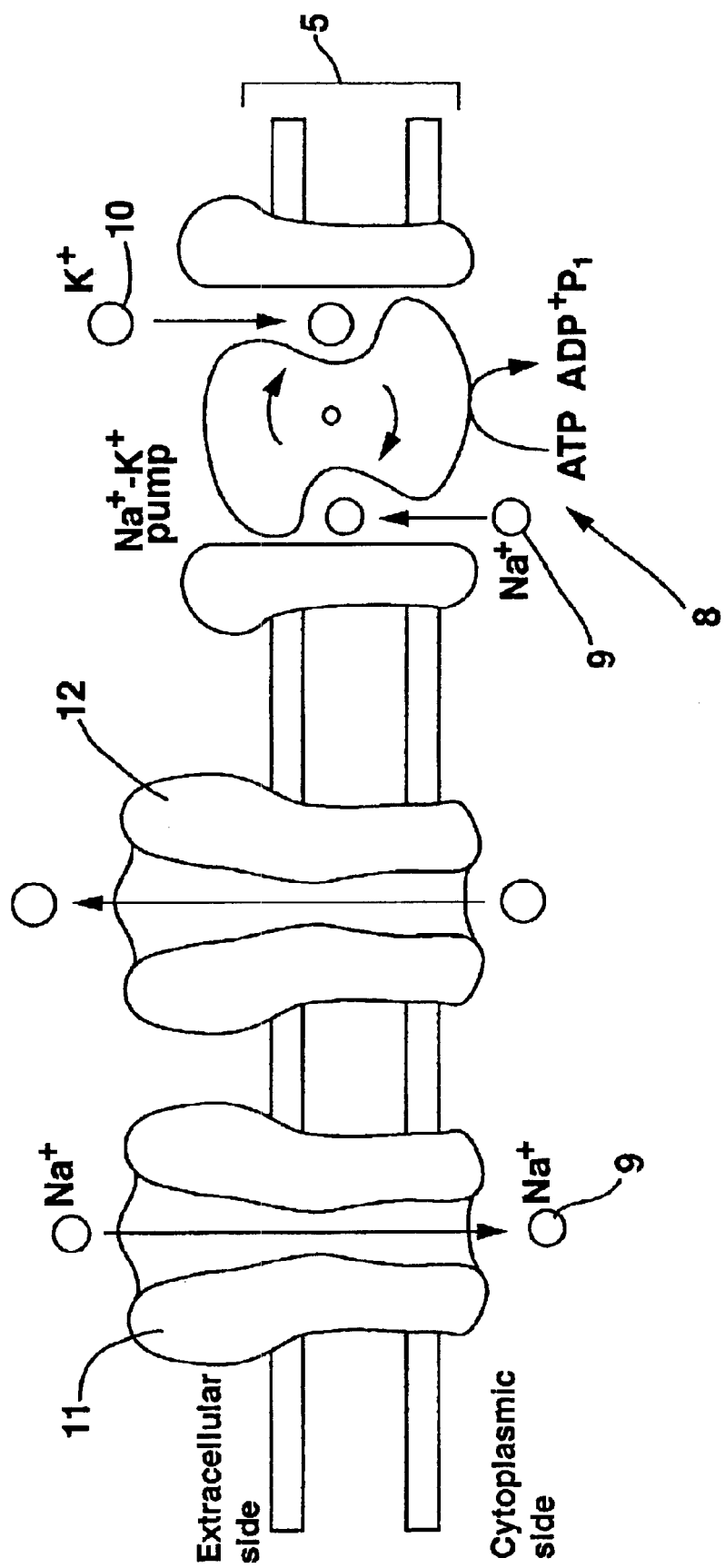
FIG. 2 is a schematic view of the chemical pumps and voltage dependent channels in the membrane of the nerve cell of FIG. 1.
Figure 3:
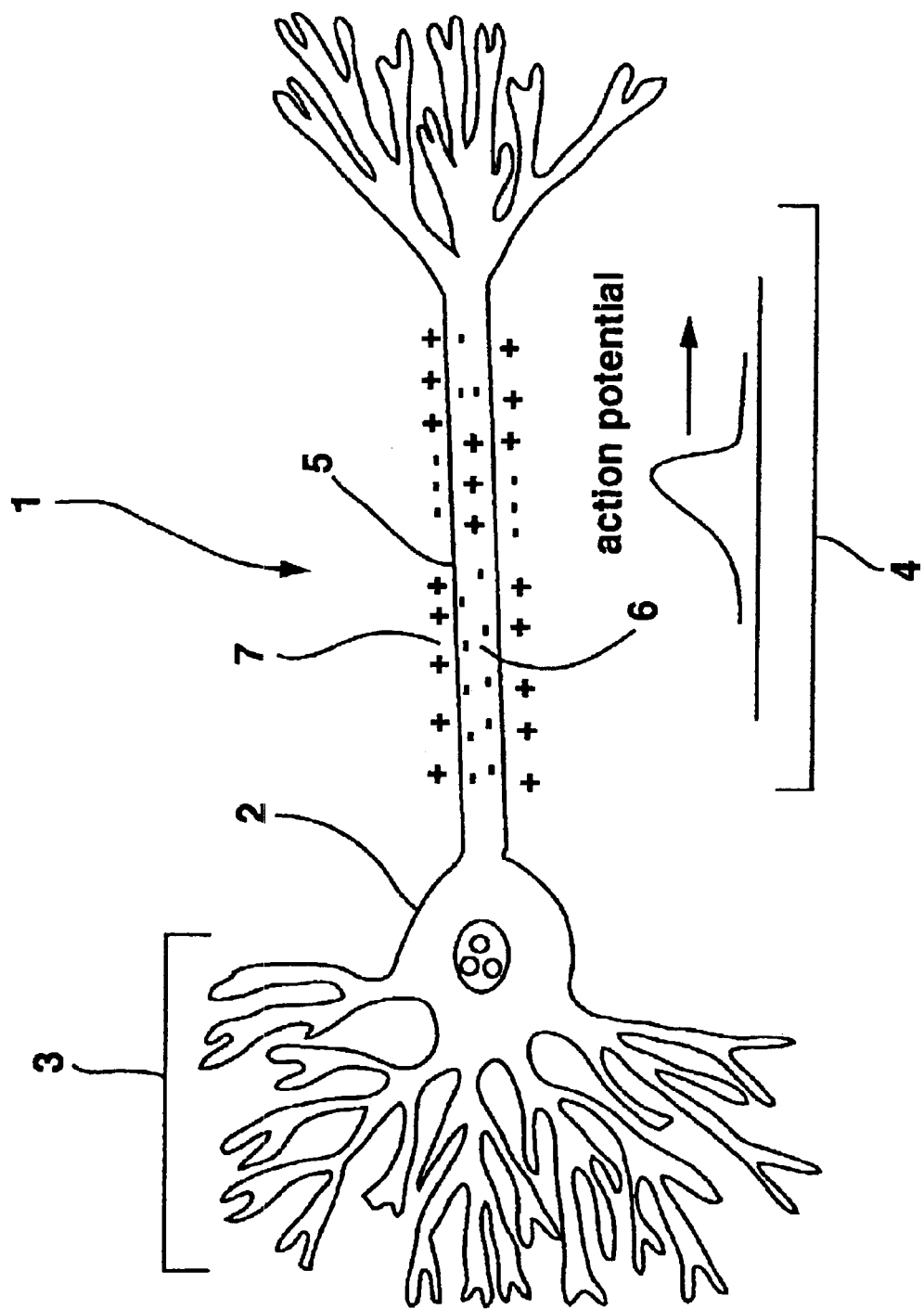
FIG. 3 is a schematic view of the nerve cell of FIG. 1 showing the propagation of an action potential.
Figure 4:
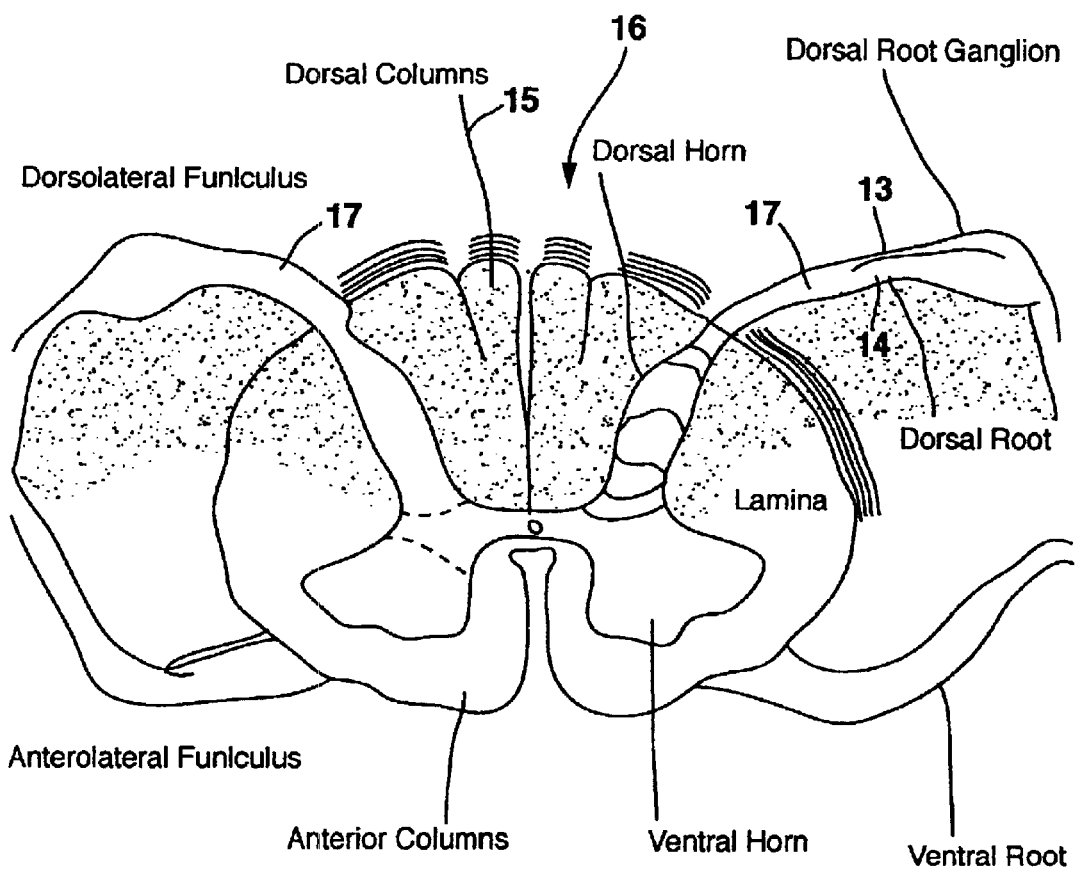
FIG. 4 is a cross-sectional view of the spine.
Figure 5:
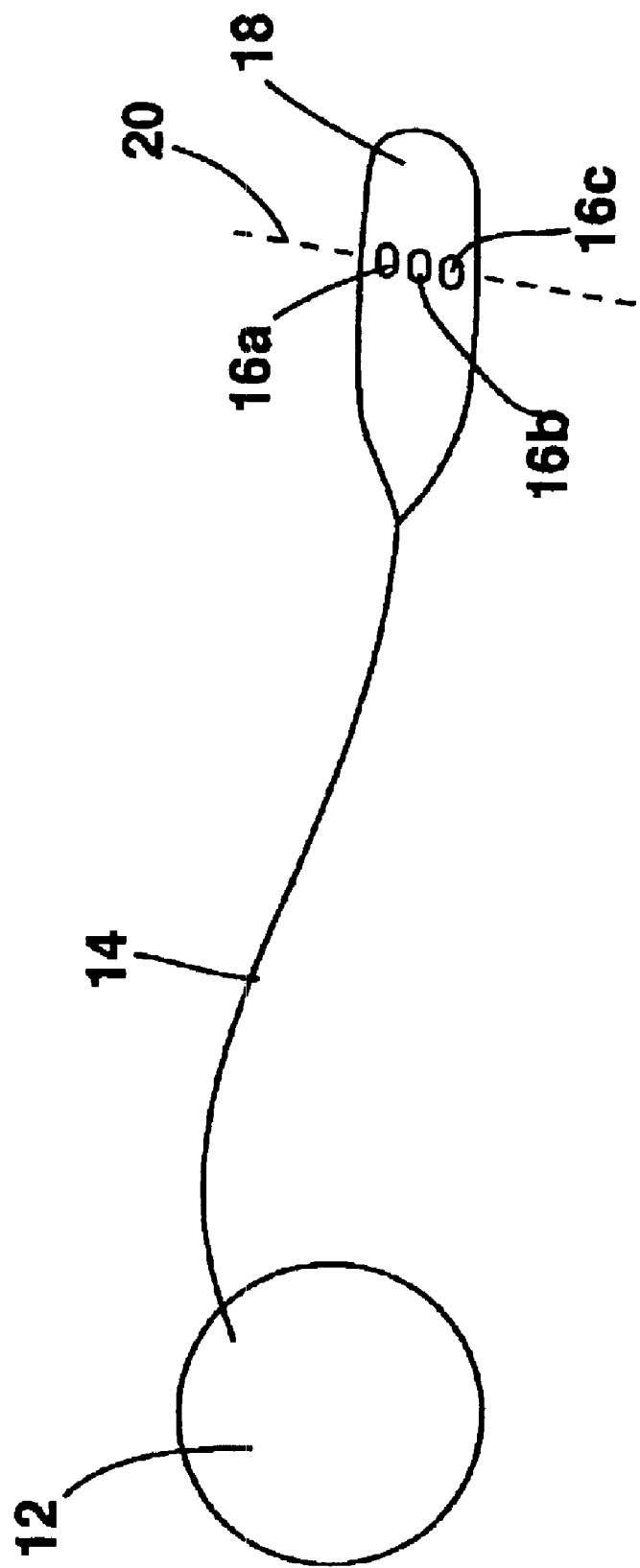
FIG. 5 is a schematic view of the present invention.

A system of the present invention is shown in FIG. 5 generally labeled 10. System 10 includes an electric signal generator that is preferably an implantable electric pulse generator (IPG) 12. IPG 12 preferably is a device having at least two channels that may be independently controllable in amplitude, frequency, timing and pulse width. In the preferred embodiment, IPG 12 has two such channels.

The pulse generator may also be a pulse generator that is connected to an implanted receiver that receives power and programming from an external transmitter by RF coupling. Such a system could be a Matrix® radio-frequency pulse generator available from Medtronic, Inc. of Minneapolis, Minn.

Alternately, an IPG 12 with three independently controllable channels can be used. In another alternate embodiment, IPG 12 may have a single channel. Such a system could be an Itrel® implantable pulse generator available from Medtronic, Inc. of Minneapolis, Minn. It is also to be understood that IPG 12 may be any device providing electrical signals whether or not those signals are electrical pulses. For example, IPG 12 may, instead of providing electrical pulses, provide electrical signals of varying amplitude and frequency such as sinusoidal waves or other relatively continuous signals.

IPG 12 is electrically connected to a lead 14 for applying stimulation pulses. Lead 14 has a series of electrodes 16a,b,c arranged on a line 20 on a paddle 18. In the preferred embodiment, electrodes 16 are located along line 20 so that when lead 14 is implanted in a patient along a patient's spinal cord, line 20 is transverse to the axis of the spinal cord. In an alternate embodiment, electrodes 16a,b,c are located along a line 20' that is parallel to the axis of the spinal cord. In either embodiment, electrode 16b is located between electrodes 16a and 16c.

In the embodiment where IPG 12 has one channel, electrodes 16a,c are attached to one output of IPG 12, while electrode 16b is connected to the other output. In the embodiment where IPG 12 has two or more channels, electrode 16b is attached to the output the channels have in common, while each electrode 16a,c is attached to the non-common output of a different channel.

In operation, lead 14 is implanted epidurally by techniques well known to those in the art and advanced to a desired location along the patient's spinal column. In this position, with the preferred embodiment of lead 14, line 20 containing electrodes 16a,b and c is located transverse to the axis of the spinal cord.

With lead 14 in place and connected to IPG 12, a pulse pattern according to the present invention is applied to electrodes 16 as will be described hereafter. This pulse pattern will produce the desired objective of preferentially stimulating the dorsal column fibers while inhibiting the stimulation of the dorsal root fibers.

Figure 6:
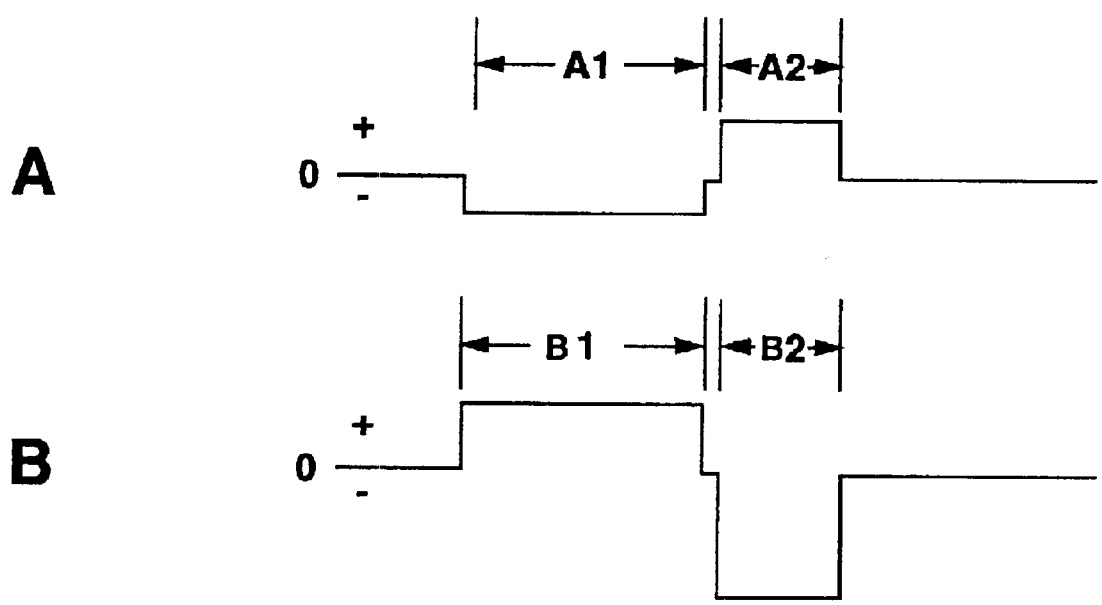
FIG. 6 is a graphic representation of the signals applied to the electrodes of the preferred embodiment of the present invention.

The pulse pattern presented to electrodes 16 is shown in FIG. 6. The pulse pattern presented to electrodes 16a,c is labeled "A". The simultaneous pulse pattern of opposite sign presented to electrode 16b is labeled "B".

Pulse pattern "A" has two parts, a depolarizing (cathodic) pre-pulse (DPP) labeled A1 followed by an anodic pulse A2. The DPP A1 should desensitize membranes of the neural tissue to be affected by the stimulation pulse A2. Experience has shown that an effective DPP A1 is about 500 µs long and has an amplitude of about 90% of the threshold amplitude for a 500 µs pulse. The DPP A1 should be opposite in sign to the stimulation pulse A2 as will be described hereafter. Although a specific DPP A1 has been described, any DPP shape that results in desensitization of the membranes of neural tissue being stimulated may be used and is within the scope of the invention.

Immediately after the pre-pulse A1, an anodic stimulation pulse A2 is applied. Stimulation pulse A2 has sufficient amplitude and duration to greatly inhibit the production of action potentials in neural tissue near electrodes 16a,c. The operation of such a stimulation pulse through the configuration of lead 14 may preferably apply a concept known as "transverse tripolar stimulation" that is explained in detail in U.S. Pat. No. 5,501,703 issued to Jan Holsheimer and Johannes J. Struijk on Mar. 26, 1996 entitled "Multichannel Apparatus for Epidural Spinal Cord Stimulator", the teachings of which are incorporated by reference in its entirety.

Pulse pattern "B" also has two parts, an anodic hyperpolarizing pre-pulse (HPP) B1 followed by a cathodic pulse B2. The HPP B1 should sensitize the cell membranes of the neural tissue to be affected by the stimulation pulse B2. Because all current flows between electrode 16b and electrodes 16a,c, the current of pulse B1 is identical to the sum of the currents of pulses A1 at electrodes 16a and 16c and simultaneous. Likewise, the current of pulse B2 is identical to the sum of the currents of A2 at electrodes 16a and 16c and simultaneous. In addition, pulses A1 and A2 should be opposite in sign to pulses B1 and B2, respectively. Because DPP A1 is about 500 µs long, HPP B1 is also about 500 µs long. Although a specific HPP B1 has been described, any HPP shape that results in sensitization of the membranes of neural tissue being stimulated may be used and is within the scope of the invention. Immediately after the HPP B1, a cathodic pulse B2 is applied. Pulse B2 has sufficient amplitude and duration to generate action potentials in neural tissue near electrode 16b.

To avoid "anodal break excitation", the duration and the magnitude of the hyperpolarizing pulse A2 might have to be limited to avoid activation of nerve cells at the end of this pulse. Alternately, the trailing edge of the pulse might need to be ramped down (c.f., Z. P. Fang and J. T. Mortimer, *IEEE Trans Biomed Eng* 1991, 38:168–174; G. S. Brindley, M. D. Craggs, *J Neurol Neurosurg Psychiatry* 1980, 43:1083–1090).

In the preferred embodiment electrode 16b is placed generally over the center of the spinal cord, and consequently near the dorsal columns 15, but away from the left and right dorsal roots 17. The HPP B1 will cause the dorsal column fibers closest to electrode 16b to be hyperpolarized and therefore more susceptible to the subsequent stimulation pulse B2. Conversely, electrodes 16a and 16c are located near the nerve fibers in the dorsal roots 17. The DPP A1 will cause the nerve fibers in the dorsal roots 17 to be slightly depolarized and therefore less likely to respond to the stimulation pulse A2. As a result, stimulation of dorsal root fibers can be avoided at a higher amplitude of the stimulation pulse A2 with a DPP A1 than it could be without a DPP A1.

As can be seen in FIG. 6, in the embodiment of IPG 12 with a single channel, pre-pulses A1 and B1 are equal in time as are anodic pulse A2 and cathodic pulse B2. In the embodiment having separate channels of IPG 12 connected to 16a–b and 16b–c, stimulation pulses A2 and B2 may have different amplitudes for contacts 16a–b and 16b–c. However, these pulses should largely overlap in time to create an electrical field promoting the stimulation of dorsal column fibers and the inhibition of dorsal root fibers, according to the concept known as "transverse tripolar stimulation" and described in U.S. Pat. No. 5,501,703 and in a paper (*Med Biol Eng Comp* 1996, 34:273–279). Likewise, pre-pulses A1 and B1 should largely overlap in time to promote the sensitization of dorsal column fibers and desensitization of dorsal root fibers. When a third channel of IPG 12 is available, this channel can be connected to a contact 16a,b,c and to the metal casing of the IPG. For either case, for every stimulation pulse the invention anticipates the application of pre-pulses.

It is believed to be important to have a zero net charge to and from electrodes 16a,b,c for each stimulation pulse. This minimizes electrode degradation and cell trauma. Ordinarily, a zero net charge is accomplished by applying a charge-balancing pulse to an electrode, opposite in sign and immediately after a stimulation pulse applied to the same electrode. The charge-balancing pulse has an amplitude and duration compensating for the charge injected by the stimulation pulse. This is usually accomplished by a charge-balancing pulse having a long duration and a low amplitude.

The application of cathodic and anodic pre-pulses A1 and B1 makes it easier to achieve this zero net charge, because these pre-pulses are opposite in sign to pulses A2 and B2, respectively. Therefore, the application of a pre-pulse makes the charge-balancing pulse smaller. If pre-pulses A1 and B1 are chosen correctly, the charge-balancing pulses may be eliminated altogether.

The application of HPP and DPP has been described in connection with stimulation of neural tissue in the spinal cord. The principal of the invention can be applied to neural tissue generally where it is desired to shield certain cells from the effects of nearby cathodal stimulation. For example, it may be desirable to preferentially stimulate certain brain cells while avoiding stimulating other nearby brain cells.

In one embodiment, a lead 14 having a first electrode 16a and a second electrode 16b would be inserted in the brain and moved to the desired location with electrode 16b near the area to be preferentially stimulated and electrode 16a moved near an area that it is desirable not to stimulate or to inhibit. A hyperpolarizing pre-pulse B1 may be applied to electrode 16b and a depolarizing pre-pulse A1 applied to electrode 16a. These pulses may both be applied or may be applied in the alternative, that is, either a hyperpolarizing pre-pulse B1 or a depolarizing pre-pulse A1 may be applied to electrode 16b.

In a variant of this embodiment, a lead 14 having two outside electrodes 16a,c and a center electrode 16b would be inserted in the brain and moved to the desired location with electrode 16b near the area to be preferentially stimulated and electrodes 16a,c moved near the areas that it is desirable not to stimulate or to inhibit. A hyperpolarizing pre-pulse B1 may be applied to electrode 16b and a depolarizing pre-pulse A1 applied to electrodes 16a,c. These pulses may both be applied or may be applied in the alternative.

In a variant of this embodiment, as before, a lead 14 having two outside electrodes 16a,c and a center electrode 16b would be inserted in the brain and moved to the desired location. In this variant, electrode 16b is placed near the area to be preferentially inhibited while electrodes 16a,c are moved near the areas that it is desirable to stimulate. A depolarizing pre-pulse A1 is sent to electrode 16b while a hyperpolarizing pre-pulse B1 is sent to electrodes 16a,c.

In another embodiment, a lead 14 having two outside electrodes 16a,c and a center electrode 16b would be placed on or near the surface of the brain, for example, on the cortex, and moved to the desired location with electrode 16b near the area to be preferentially stimulated and electrodes 16a,c moved near the areas that it is desirable not to stimulate or to inhibit. The lead is then operated as described above in connection with stimulating spinal cord tissue. In this embodiment, the lead may be placed either sub-durally or epidurally.

In any of the embodiments of the lead having three electrodes, whether for use on the spine, in the brain or on peripheral nerve, the electrodes may be arranged along a single line or may be arranged in a two or three-dimensional array, that is, so that only two electrodes are on a single line.

Likewise, it may be desirable to preferentially stimulate certain nerve fibers in a peripheral nerve or spinal nerve root while avoiding stimulating other nearby nerve fibers. In one embodiment, a lead 14 having two outside electrodes 16a,c and a center electrode 16b would be placed around part of a nerve bundle so that line 20 is transverse to the axis of the nerve bundle and electrode 16b is near the nerve fibers to be preferentially stimulated. The lead is then operated as described above in connection with stimulating spinal cord tissue.

In another embodiment, a number of electrodes are placed at the inside of a nerve cuff, transverse to the axis of the nerve bundle. One electrode near the nerve fibers to be preferentially stimulated is selected as the electrode 16b, while the neighboring ones are selected as electrodes 16a,c. The lead is then operated as described above in connection with stimulating spinal cord tissue.

While this invention has been described with reference to illustrative embodiments, this description is not intended to be constructed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

I claim:

1. A method of preparing neural tissue of the brain for subsequent electrical stimulation comprising the steps of:

placing first, second and third electrodes in close proximity to tissue of a patient's brain;

applying a hyperpolarizing electrical pre-pulse to the tissue through the first electrode wherein the tissue is more susceptible to subsequent electric stimulation;

applying a depolarizing electrical pre-pulse to the tissue through a second electrode wherein the tissue near the second electrode is less susceptible to subsequent electric stimulation; and applying depolarizing electrical pre-pulse to the tissue through a third electrode wherein the tissue near the third electrode is less susceptible to subsequent electric stimulation.

2. The method of claim 1 wherein the step of placing first, second and third electrodes in close proximity to tissue of a patient's brain includes placing the first electrode in tissue of a patient's brain.

3. The method of claim 2 wherein the step of placing first, second and third electrodes in close proximity to tissue of a patient's brain includes placing the second electrode in tissue of a patient's brain.

4. The method of claim 3 wherein the step of placing first, second and third electrodes in close proximity to tissue of a patient's brain includes placing the third electrode in tissue of a patient's brain.

5. The method claim 4 further comprising the steps of:
implanting a source of electrical pulses within the patient's body; and
electrically connecting the source of electrical pulses to the first, second and third electrodes.

6. The method of claim 3 further comprising the steps of:
implanting a source of electrical pulses within the patient's body; and
electrically connecting the source of electrical pulses to the first, second and third electrodes.

7. The method of claim 2 further comprising the steps of:
implanting a source of electrical pulses within the patient's body; and
electrically connecting the source of electrical pulses to the first, second and third electrodes.

8. The method of claim 1 wherein the step of placing first, second and third electrodes in close proximity to tissue of a patient's brain includes placing the first electrode on the surface of a patient's brain.

9. The method of claim 8 wherein the step of placing first, second and third electrodes in close proximity to tissue of a patient's brain includes placing the second electrode on the surface of a patient's brain.

10. The method of claim 9 wherein the step of placing first, second and third electrodes in close proximity to tissue of a patient's brain includes placing the third electrode on the surface of a patient's brain.

11. The method of claim 10 further comprising the steps of:
implanting a source of electrical pulses within the patient's body; and
electrically connecting the source of electrical pulses to the first, second and third electrodes.

12. The method of claim 9 further comprising the steps of:
implanting a source of electrical pulses within the patient's body; and
electrically connecting the source of electrical pulses to the first, second and third electrodes.

13. The method of claim 8 further comprising the steps of:
implanting a source of electrical pulses within the patient's body; and
electrically connecting the source of electrical pulses to the first second and third electrodes.

14. The method of claim 1 wherein the step of placing first, second and third electrodes in close proximity to tissue of a patient's brain includes placing the first electrode near the surface of a patient's brain.

15. The method of claim 14 wherein the step of placing first, second and third electrodes in close proximity to tissue of a patient's brain includes placing the second electrode near the surface of a patient's brain.

16. The method of claim 15 wherein the step of placing first, second and third electrodes in close proximity to tissue of a patient's brain includes placing the third electrode near the surface of a patient's brain.

17. The method of claim 16 further comprising the steps of:
implanting a source of electrical pulses within the patient's body; and
electrically connecting the source of electrical pulses to the first, second and third electrodes.

18. The method of claim 15 further comprising the stops of:
implanting a source of electrical pulses within the patient's body; and
electrically connecting the source of electrical pulses to the first, second and third electrodes.

19. The method of claim 14 further comprising the steps of:
implanting a source of electrical pulses within the patient's body; and
electrically connecting the source of electrical pulses to the first, second and third electrodes.

20. A method of preparing neural tissue of the brain for subsequent electrical stimulation comprising the steps of:
providing a source of electrical pulses;
providing a first electrode;
providing an electrical return path;
connecting the first electrode to the source of electrical pulses;
placing the first electrode in tissue of a patient's brain;
applying a hyperpolarizing electrical pre-pulse to the tissue through the first electrode wherein the tissue is more susceptible to subsequent electric stimulation; and
applying a subsequent depolarizing electrical pulse to the tissue through the first electrode.

21. The method of claim 20, wherein the step of providing an electrical return path includes the step of providing an electrical return path that includes a second electrode.

22. The method of claim 20 wherein the step of providing an electrical return path includes the step of providing an electrical return path that includes the source of electrical pulses.

23. The method of claim 20 wherein the step of providing a first electrode includes the step of providing a second electrode spaced from the first electrode and further comprising the step of connecting the second electrode to the source of electrical pulses.

24. The method of claim 23 further comprising the step of:
applying a depolarizing electrical pre-pulse to the tissue through the second electrode wherein the tissue near the second electrode is less susceptible to subsequent electric stimulation.

25. The method of claim 20 further comprising the step of implanting the source of electrical pulses within the patient's body.

26. A method of preparing neural tissue of the brain for subsequent electrical stimulation comprising the step of:
providing a source of electrical pulses;
providing a first electrode;
providing an electrical return path:
connecting the first electrode to the source of electrical pulses;
placing the first electrode in tissue of a patient's brain; and
applying a hyperpolarizing electrical pre-pulse to the tissue through the first electrode wherein the tissue is more susceptible to subsequent electric stimulation;

wherein the step of providing a first electrode includes the step of providing a second electrode spaced from the first electrode and further comprising the step of connecting the second electrode to the source of electrical pulses; p1 applying a depolarizing electrical pre-pulse to the tissue through the second electrode wherein the tissue near the second electrode is less susceptible to subsequent electric stimulation; and wherein the step of providing a first electrode and a second electrode spaced from the first electrode includes the step of providing a third electrode spaced from the first and second electrodes and further comprising the step of connecting the third electrode to the source of electrical pulses.

27. The method of claim 26 further comprising the step of: applying a depolarizing electrical pre-pulse to the tissue through the third electrode wherein the tissue near the third electrode is less susceptible to subsequent electric stimulation.

28. The method of claim 26 further comprising the step of: applying a hyperpolarizing electrical pre-pulse to the tissue through the third electrode wherein the tissue near the third electrode is more susceptible to subsequent electric stimulation.

29. A method of preparing neural tissue of the brain for subsequent electrical stimulation comprising the steps of:
providing a source of electrical pulses;
providing a first electrode;
providing an electrical return path;
connecting the first electrode to the source of electrical pulses;
placing the first electrode on the surface of a patient's brain;
applying a hyperpolarizing electrical pre-pulse to the tissue through the first electrode wherein the tissue is more susceptible to subsequent electric stimulation;
applying a subsequent subthreshold depolarizing electrical pre-pulse to the tissue through the first electrode.

30. The method of claim 29 wherein the step of providing an electrical return path includes the step of providing an electrical return path that includes a second electrode.

31. The method of claim 29 wherein the step of providing an electrical return path includes the step of providing an electrical return path that includes the source of electrical pulses.

32. The method of claim 29 wherein the step of providing a first electrode includes the step of providing a second electrode spaced from the first electrode and further comprising the step of connecting the second electrode to the source of electrical pulses.

33. The method of claim 32 further comprising the step of: applying a depolarizing electrical pre-pulse to the tissue through the second electrode wherein the tissue near the second electrode is less susceptible to subsequent electric stimulation.

34. The method of claim 33 wherein the step of providing a first electrode and a second electrode spaced from the first electrode includes the step of providing a third electrode spaced from the first and second electrodes and further comprising the step of connecting the third electrode to the source of electrical pulses.

35. The method of claim 34 further comprising the step of: applying a depolarizing electrical pre-pulse to the tissue through the third electrode wherein the tissue near the third electrode is less susceptible to subsequent electric stimulation.

36. The method of claim 34 further comprising the step of: applying a hyperpolarizing electrical pre-pulse to the tissue through the third electrode wherein the tissue near the third electrode is more susceptible to subsequent electric stimulation.

37. The method of claim 29 further comprising the step of implanting the source of electrical pulses within the patient's body.

38. A method of preparing neural tissue of the brain for subsequent electrical stimulation comprising the steps of:
providing a source of electrical pulses;
providing a first electrode, a second electrode spaced from the first electrode and a third electrode spaced from the first electrode opposite the second electrode so that the first electrode is generally between the second and third electrodes;
providing an electrical return path;
connecting the first, second and third electrodes to the source of electrical pulses;
placing the first, second and third electrodes within a patient's body in a patient's brain;
applying a hyperpolarizing electrical pre-pulse to the tissue through the first electrode wherein the tissue is more susceptible to subsequent electric stimulation;
applying a depolarizing electrical pre-pulse to the tissue through the second and third electrodes wherein the tissue near the second and third electrodes is less susceptible to subsequent electric stimulation.

39. The method of claim 38 further comprising the step of applying a subsequent depolarizing electrical pulse to the tissue through the first electrode.

40. The method of claim 39 further comprising the step of implanting the source of electrical pulses within the patient's body.

41. A method of preparing neural tissue of the brain for subsequent electrical stimulation comprising the steps of:
placing first, second and third electrodes in close proximity to tissue of a patient's brain;
applying a hyperpolarizing electrical pre-pulse to the tissue through the first electrode wherein the tissue is more susceptible to subsequent electric stimulation;
applying a depolarizing electrical pre-pulse to the tissue through a second electrode wherein the tissue near the second electrode is less susceptible to subsequent electric stimulation; and
applying a hyperpolarizing electrical pre-pulse to the tissue through the third electrode wherein the tissue near the third electrode is more susceptible to subsequent electric stimulation.

42. The method of claim 41 wherein the step of placing first, second and third electrodes in close proximity to tissue of a patient's brain includes placing the first electrode in tissue of a patient's brain.

43. The method of claim 42 wherein the step of placing first, second and third electrodes in close proximity to tissue of a patient's brain includes placing the second electrode in tissue of a patient's brain.

44. The method of claim 43 wherein the step of placing first, second and third electrodes in close proximity to tissue of a patient's brain includes placing the third electrode in tissue of a patient's brain.

45. The method of claim 44 further comprising the steps of:
implanting a source of electrical pulses within the patient's body; and electrically connecting the source of electrical pulses to the first, second and third electrodes.

46. The method of claim 43 further comprising the steps of:

implanting a source of electrical pulses within the patient's body; and electrically connecting the source of electrical pulses to the first, second and third electrodes.

47. The method of claim 42 further comprising the steps of:

implanting a source of electrical pulses within the patient's body; and electrically connecting the source of electrical pulses to the first, second and third electrodes.

48. The method of claim 41 wherein the step of placing first, second and third electrodes in close proximity to tissue of patient's brain includes placing the first electrode on the surface of a patient's brain.

49. The method of claim 48 wherein the step of placing first, second and third electrodes in close proximity to tissue of a patient's brain includes placing the second electrode on the surface of a patient's brain.

50. The method of claim 49 wherein the step of placing first, second and third electrodes in close proximity to tissue of a patient's brain includes placing the third electrode on the surface of a patient's brain.

51. The method of claim 50 further comprising the steps of:

implanting a source of electrical pulses within the patient's body; and electrically connecting the source of electrical pulses to the first, second and third electrodes.

52. The method of claim 49 further comprising the steps of:

implanting a source of electrical pulses within the patient's body; and electrically connecting the source of electrical pulses to the first, second and third electrodes.

53. The method of claim 48 further comprising the steps of:

implanting a source of electrical pulses within the patient's body; and electrically connecting the source of electrical pulses to the first, second and third electrodes.

54. The method of claim 41 wherein the step of placing first, second and third electrodes in close proximity to tissue of a patient's brain includes placing the first electrode near the surface of a patient's brain.

55. The method of claim 54 wherein the step of placing first, second and third electrodes in close proximity to tissue of a patient's brain includes placing the second electrode near the surface of a patient's brain.

56. The method of claim 55 wherein the step of placing first, second and third electrodes in close proximity to tissue of a patient's brain includes placing the third electrode near the surface of a patient's brain.

57. The method of claim 56 further comprising the steps of:

implanting a source of electrical pulses within the patient's body; and electrically connecting the source of electrical pulses to the first, second and third electrodes.

58. The method of claim 55 further comprising the steps of:

implanting a source of electrical pulses within the patient's body; and electrically connecting the source of electrical pulses to the first, second and third electrodes.

59. The method of claim 54 further comprising the steps of:

implanting a source of electrical pulses within the patient's body; and electrically connecting the source of electrical pulses to the first, second and third electrodes.

* * * * *

UNITED STATES PATENT AND TRADEMARK OFFICE
CERTIFICATE OF CORRECTION

PATENT NO. : 6,892,097 B2
DATED : May 10, 2005
INVENTOR(S) : Jan Holsheimer

It is certified that error appears in the above-identified patent and that said Letters Patent is hereby corrected as shown below:

Column 10,
Line 57, reads "...comprising the step of: ..." should read -- ...comprising the steps of: ... --.

Column 11,
Line 5, reads "...pulses; p1applying..." should read -- ...pulses; applying... --.

Signed and Sealed this

Twentieth Day of December, 2005

JON W. DUDAS
*Director of the United States Patent and Trademark Office*